United States Patent [19]

Olsen et al.

[11] Patent Number: 4,591,485
[45] Date of Patent: May 27, 1986

[54] METHOD AND APPARATUS FOR SONICATING ARTICLES

[75] Inventors: William L. Olsen, Warwick, N.Y.; John O. Freeborn, New Fairfield, Conn.; Linnea J. Shaver, Sloatsburg; Janice J. Kelemen, Central Valley, both of N.Y.

[73] Assignee: International Paper Company, New York, N.Y.

[21] Appl. No.: 564,424

[22] Filed: Dec. 22, 1983

[51] Int. Cl.⁴ .............................................. A61L 2/02
[52] U.S. Cl. ........................................ 422/20; 422/24; 422/31; 422/128; 53/425; 134/1; 134/10; 134/15; 239/102
[58] Field of Search ................... 422/20, 24, 300, 302, 422/304, 128, 33, 31; 239/102; 53/425, 426; 134/1, 15, 10, 12

[56] References Cited

U.S. PATENT DOCUMENTS

| | | | |
|---|---|---|---|
| Re. 30,870 | 2/1982 | Inoue | 137/13 |
| 2,558,066 | 6/1951 | Wedler | 260/233 |
| 3,383,831 | 5/1968 | Goldsmith et al. | 53/167 |
| 3,491,778 | 1/1970 | Lehnert et al. | 134/64 |
| 3,613,701 | 10/1971 | Ando | 134/64 |
| 3,929,409 | 12/1975 | Buchner et al. | 422/128 |
| 3,966,120 | 6/1976 | Furgalus et al. | 239/102 |
| 4,086,057 | 4/1978 | Everett | 422/128 |
| 4,193,842 | 3/1980 | Rushing | 162/199 |
| 4,316,580 | 2/1982 | Bodai | 239/466 |
| 4,326,553 | 4/1982 | Hall | 239/102 |
| 4,401,114 | 8/1983 | Lwoff et al. | 128/200.14 |
| 4,402,458 | 9/1983 | Lierke et al. | 239/102 |
| 4,424,188 | 1/1984 | DiGeronimo | 422/20 |

Primary Examiner—David L. Lacey
Assistant Examiner—Titus B. Ledbetter, Jr.
Attorney, Agent, or Firm—Richard J. Ancel

[57] ABSTRACT

A method and apparatus are provided for sonicating an article such that the liquid used as the sonication medium cannot recontaminate the article. A sonication medium in the form of a film of liquid is streamed over the article. A probe of a sonic horn is positioned in sonic energy transfer relationship to the sonication medium next to the article. Sound waves transmitted through the sonication medium dislodge particles from the article and into the sonication medium. The sonication medium carrying dislodged particles is drained away after passing the probe of the sonic horn. A subsequent sterilization means can be used to further clean the article. The article can be a web of packaging material used subsequent to sterilization for forming into individual containers for the aseptic packaging of foodstuffs or the like.

19 Claims, 1 Drawing Figure

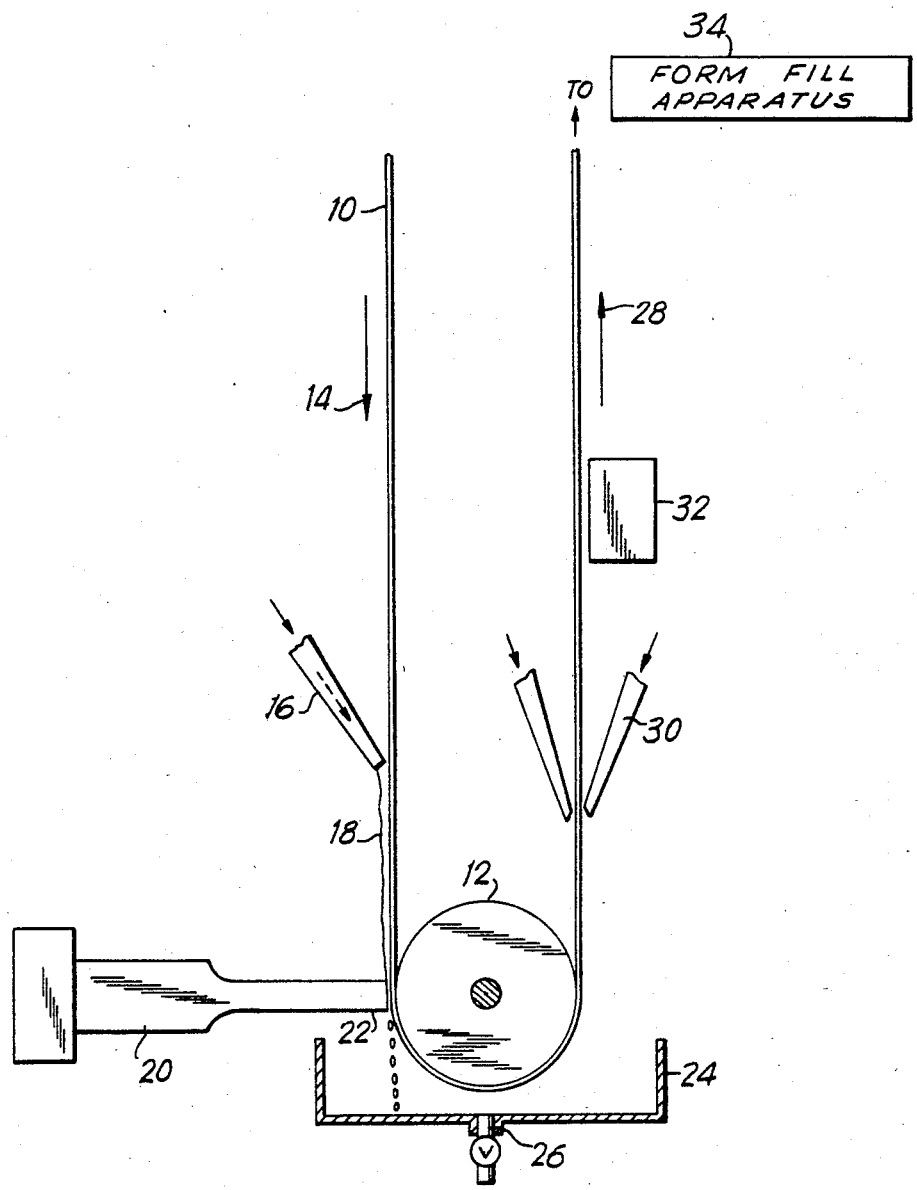

4,591,485

METHOD AND APPARATUS FOR SONICATING ARTICLES

FIELD OF THE INVENTION

This invention relates to the art of using ultrasonic sound waves to clean articles and particularly, to a method and apparatus for such ultrasonic cleaning of a moving web of paper or the like.

BACKGROUND OF THE INVENTION

The generally accepted practice for sonicating articles is to immerse or partially immerse those articles in a liquid bath. A sonic horn, also immersed in the bath, generates ultrasonic sound waves through the liquid medium of the bath. The articles are cleaned by the sound waves dislodging small particles from the articles.

One problem with the generally accepted configuration is recontamination. Recontamination occurs when dislodged particles redeposit themselves on articles being cleaned in a sonic bath.

Avoidance of recontamination is particularly important when ultrasonic cleaning is used in a process for sterilization. For example, commonly assigned U.S. Pat. No. 4,424,188 issued Jan. 3, 1984, which is incorporated by reference herein, discloses the use of ultrasonic irradiation in conjunction with ultraviolet irradiation to substantially reduce the number of viable microorganisms on a paperboard laminate surface, such as is used for the aseptic packaging of foodstuffs. In the '188 patent it is further disclosed that in a sterilization sequence where ultrasonic irradiation is followed by ultraviolet irradiation, the reduction in microorganisms is significantly greater than when performed in the reverse order, that is, where ultraviolet is followed by ultrasonic irradiation. The probable explanation for the significant reduction in microorganisms when ultrasonic irradiation is followed by ultraviolet irradiation is that the ultrasonic treatment dislodges and positions the microorganisms so that they are exposed to maximum ultraviolet irradiation.

In the '188 patent, the paperboard laminate to be sonicated is either fully or partially immersed in a water bath and subjected to sonication within the bath. However, using this bath configuration, there is a tendency to redistribute microorganisms over the paperboard laminate. Even sterile paperboard laminate sonicated in a used bath will become contaminated. Thus, when using the bath configuration, there is a need for constant flushing of the bath with sterile water. In addition, immersion of the paperboard laminate in a bath results in wicking (soaking up of water by capillary action) into the edge of the board possibly leading to further contamination in addition to damaging the board.

SUMMARY OF THE INVENTION

According to the present invention, a sonication medium is streamed over an article. A sonic horn is positioned in sonic energy transfer relationship to the sonication medium streamed over the article. The sonic horn produces sound waves which dislodge particles from the article into the sonication medium or places those particles in a position more accessible to sterilization. After passing the sonic horn, the sonication medium carrying the dislodged particles from the article is collected below the sonic horn. In a preferred embodiment, paperboard laminate used to make containers for the aseptic packaging of foodstuffs is sonicated. The sonicated web can then be treated with a sterilization means, such as ultraviolet irradiation or a chemical biocide, before forming the web into individual packages used in the aseptic packaging of foodstuffs.

The present invention enables the sonication of an article without redistributing dislodged particles over the article. The present invention also minimizes consumption of fresh liquid used as a sonication medium. Further, the present invention minimizes soaking of the article in the sonication medium, which soaking can cause recontamination and damage to the article.

BRIEF DESCRIPTION OF THE FIGURE

The FIGURE illustrates the sonication configuration of the present invention and how this invention can be used in a continuous process for the sterilization of a moving web of material, which may be subsequently formed into individual containers for foodstuffs or the like.

DESCRIPTION OF THE PREFERRED EMBODIMENT

Referring now to the FIGURE, a web of material 10 is fed under a roller 12 in the direction of arrow 14. A liquid source 16 streams a film 18 of liquid over the surface of web 10 which will form the inner, food contacting surface of a container formed from the web for the aseptic packaging of foodstuffs. The film 18 is used as a sonication medium and must be thin enough to transmit sound waves from a sonic horn 20 to the surface of the web. A probe 22 of sonic horn 20 is set in a sonic energy transfer relationship to film 18 below the liquid source 16. The sound waves produced by the sonic horn 20 and transmitted through the sonication medium serve to dislodge particles, such as microorganisms or spores thereof, from the surface of web 10. Those particles are either carried away by the sonication medium or are put in a position on the web so that the particles are more accessible to sterilization. For example, microorganisms can be dislodged from crevices in the webs, making those microorganisms more accessible to sterilization by ultraviolet irradiation. Typically, the liquid used as the sonication medium is sterile water. However, the sonication medium can contain a chemical biocide. Although the web 10 is vertically oriented in the FIGURE, the web can be oriented at any angle as long as the sonication medium carrying dislodged particles can drain off the web after passing by the sonic horn.

The sonication medium which has passed by the sonic horn and carries dislodged particles is caught by tank 24. Drain 26 is located at the bottom of tank 24 to direct the sonication medium containing dislodged particles to a waste pipe or to a filter for recycling to liquid source 16.

Because the dislodged particles are constantly being carried away by the sonication medium, there is no recontamination of the web as in the case of a bath sonication configuration and no need to constantly flush the bath with fresh sonication medium. In addition, because contact between the web and the sonication medium is minimized, the risk of wicking, causing recontamination and damage to the web, is reduced.

As web 10 moves upwardly in the direction of arrow 28 in the FIGURE, web 10 passes a drying means, such as air knives 30. Web 10 then moves past a sterilization means 32, such as a source of ultraviolet irradiation or a chemical biocide. Thereafter, the web 10 passes into a form-fill apparatus 34 which, in general, forms tubes from the web, fills them with a sterile food product, and cuts and seals them to form individual containers of an aseptically packaged product. One form-fill system is illustrated in U.S. Pat. No. 3,789,569.

EXAMPLE

Experimental work was performed to demonstrate the degree of microorganism reduction in an inoculated board after treatment with an ultrasonic/ultraviolet sterilization sequence using the skimming configuration of the present invention.

The degree of sterilization can be expressed as the log reduction of microorganisms which is calculated as follows:

$$\text{Log Reduction } (\Delta \log) = \log \frac{\text{Inoculum}}{\text{Total Value Spores Remaining After Sterilization Procedure}}$$

Sterile 2 inch×2 inch (50.8 mm.×50.8 mm.) boards were inoculated with 20–100 μl of spore suspension of *Bacillus subtilis* var. niger (*B. globigii*) giving a 0.5–1.0×10$^8$ inoculum. The boards were allowed to dry for 30 minutes.

The boards had the following laminate construction: (low density) polyethylene (external layer)/paperboard/Surlyn/aluminum foil/Surlyn/(low density) polyethylene (internal layer). (Surlyn is DuPont's trademark for an ionically cross-linked thermoplastic resin that is derived from ethylene/methacrylic acid copolymer).

A wide sonic horn was used to accommodate wide packaging board stock. The horn was a 9 in.×½ in. (22.86 cm.×1.27 cm.) Branson Ti horn (working area=4.5 in.$^2$ (29.03 cm.$^2$)) and was driven by a Branson Model 184V ultrasonic power supply equipped with a #102 converter (transducer). Boosters were available with various input/output energy ratios: 1:0.5 (blue), 1:0.6 (purple), 1:1 (green), and 1:1.5 (gold). The sonication equipment operates at 20 KHz and has a maximum power output of 900 watts.

Using the sonication configuration of the present invention, a small amount of sterile water was streamed over the board surface. The board surface was then skimmed under the activated probe. The film of sterile water was 2–3 mm. thick and the probe was held 1–3 mm. away from the web in the film of sterile water. The probe was activated at maximum power output (900 watts) for 3–4 seconds.

Ultraviolet irradiation of the boards was performed using a high intensity lamp from Brown Boveri Corporation, Switzerland (Model UV-C 13-50). This lamp is operable in the C region of the ultraviolet spectrum which emits energy essentially in the region of 254 nanometers.

The log reduction using all available boosters is shown in Table 1. This system was able to achieve a log reduction of about 6 using the 1:1.5, 1:1.0, and 1:0.6 boosters and a log reduction greater than about 7 using the 1:0.5 booster.

TABLE 1

Skimming (3–4 sec. at maximum power output)
9 in. × ½ in. (22.86 cm. × 1.27 cm.) probe
UV Irradiation: 2 cm./15 sec.
Organism: *B. globigii*

| Booster | Δ Log |
|---|---|
| 1:1.5 | 5.9 |
| 1:1.0 | 5.7 |
| 1:0.6 | 5.9 |
| 1:0.5 | 7.2 |

COMPARATIVE EXAMPLE

Table 2 shows the results obtained employing the prior art method according to which the wide probe sonic horn was placed in a water bath. Only the 1:0.5 and 1:0.6 boosters could be used in the bath since higher ratio boosters overloaded the power supply when the horn was placed in the water bath. This system was able to achieve a log reduction of greater than 6. However, there is a tendency to redistribute spores over the board during sonication. Even a sterile paperboard laminate sonicated in a used bath will become contaminated. Thus, when using the bath configuration, there is a need for constant flushing of the bath with sterile water.

TABLE 2

400 ml. water bath (2–3 sec. at maximum power output)
9 in. × ½ in. (22.86 cm. × 1.27 cm.) probe
UV Irradiation: 2 cm./15 sec.
Organism: *B. globigii*

| Booster | Δ Log |
|---|---|
| 1:0.6 | 6.3 |
| 1:0.5 | 6.5 |

Having described the invention with particular reference to the preferred form thereof, it will be apparent to those skilled in the art to which the invention pertains, that various changes and modifications can be made therein without departing from the spirit and scope of the invention as defined by the claims appended hereto.

We claim:

1. A method for sonicating articles to remove particles therefrom comprising the steps of (1) directing a moving film of a liquid medium over and in contact with a surface of an article having particles thereon, (2) placing an activated sonic horn in sonic energy transfer relationship to the liquid medium while it is still in the form of a film, so that sound waves produced by the activated sonic horn dislodge particles from the article into the liquid medium film while still on the surface of the article, the liquid medium film, which carries the dislodged particles, being withdrawn from contact with the article so that there is no contact of the liquid medium film on the article with a reservoir of the liquid medium, whereby the particles which have been dislodged from the article are not redistributed over the article by continued contact with the reservoir of liquid medium.

2. A method for sonicating a moving web of packaging material to remove particles therefrom for use in forming individual aseptic containers comprising the steps of (1) directing a moving film of a liquid medium over and in contact with at least one surface of the web having particles thereon, (2) placing an activated sonic horn in sonic energy transfer relationship to the liquid medium while it is still in the form of a film, so that sound waves produced by the activated sonic horn dislodge particles from the web into the liquid medium film on the surface of the web, the liquid medium film, which carries the dislodged particles, being withdrawn from contact with the web so that there is no contact of the liquid medium film on the web with a reservoir of the liquid medium, and becoming no longer in contact with the web surface, whereby the particles which have been dislodged from the web surface are not redistributed over the web by continued contact with the reservoir of liquid medium.

3. The method of claim 2 wherein the dislodged particles are microorganisms or spores thereof.

4. The method of claim 2 wherein the web is vertically oriented so that the liquid medium carrying dislodged particles runs off the web after passing the sonic horn, with the additional step of (3) collecting the liquid medium below the web for cleaning and subsequent reuse of the medium.

5. The method of claim 2 wherein the liquid medium is collected after falling off the web for subsequent cleaning and recycling for reuse in step (1).

6. The method of claim 2 further comprising the step of drying the web and subjecting the web to sterilization.

7. The method of claim 6 wherein the liquid medium is sterile water.

8. The method of claim 6 wherein sterilizing is carried out using ultraviolet irradiation.

9. The method of claim 6 wherein sterilizing is carried out using a chemical biocide.

10. The method of claim 6 wherein drying is carried out using air knives.

11. An apparatus for sonicating an article to remove particles therefrom comprising means for directing a moving film of a liquid medium over and in contact with a surface of an article, having particles thereon a sonic horn positioned in sonic energy transfer relationship to the liquid medium streamed over the article, means for projecting ultrasonic sound waves through the liquid medium, while the liquid medium is still in the form of a film, and dislodging particles from the article into the liquid medium by the ultra sonic sound waves while the liquid medium is still in the form of a film, the article being positioned so that the liquid medium film while still on the surface of the article, which carries the dislodged particles, is withdrawn from contact with the article so that there is no contact with the liquid medium film on the article with a reservoir of the liquid medium, whereby the particles which have been dislodged from the article surface are not redistributed over the article by continued contact with the reservoir of liquid medium.

12. The apparatus of claim 11 including means for collecting the liquid medium after it has left the article whereby the collected liquid medium may be subsequently cleaned and recycled for reuse in the apparatus.

13. The apparatus of claim 11 wherein the article to be sonicated is a web of packaging material for use in forming individual aseptic containers.

14. The apparatus of claim 13 wherein the sonic horn has a probe for sonicating the web of packaging material.

15. The apparatus of claim 14 which further comprises means for drying and sterilizing the web of material.

16. The apparatus of claim 15 wherein the means for drying comprises air knives.

17. The apparatus of claim 15 wherein the means for sterilizing comprises ultraviolet radiation.

18. The apparatus of claim 15 wherein the means for sterilizing comprises a chemical biocide.

19. The apparatus of claim 15 which further comprises a means for making individual aseptic containers from the sonicated and sterilized web of packaging material.

* * * * *